US00PP09673P

United States Patent [19]

Zaiger et al.

[11] Patent Number: Plant 9,673

[45] Date of Patent: Oct. 29, 1996

[54] PEACH TREE 'ZEE DIAMOND'

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 499,409

[22] Filed: Jul. 10, 1995

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

A new and distinct variety of peach tree with the following unique combination of desirable features that are outstanding in a new variety:

1. Heavy and regular production of large size fruit.
2. Fruit with a high degree of attractive red skin color.
3. Fruit with good flavor and eating quality.
4. Good handling and shipping quality of the fruit.
5. Vigorous semi-upright growth of tree.
6. Early maturity of the fruit.

1 Drawing Sheet

ORIGIN OF THE VARIETY

The present new variety of peach tree was originated by us in our experimental orchard located near Modesto, Calif., as an open pollinated seedling from seed of 65EC70. The selected peach seedling with the field identification number 65EC70 originated from a cross between two selected seedlings with the field identification numbers 34GA1155 and 36EB346. The female parent 34GA1155 originated from a cross between a selected seedling of May Grand Nectarine (U.S. Plant Pat. No. 2,794) crossed with a peach of unknown parentage. This selection was then crossed with an open pollinated seedling of Sam Houston Peach (non-patented). The pollen parent 36EB346 originated from a first generation cross between Tasty Gold Nectarine (U.S. Plant Pat. No. 5,623) crossed with May Crest Peach (U.S. Plant Pat. No. 4,064). We grew and maintained a large group of these open pollinated seedlings under careful observation and the present variety which evidenced distinctive desirable fruit characteristics was selected for asexual reproduction and commercialization.

ASEXUAL REPRODUCTION OF THE VARIETY

The present new variety of peach tree was asexually reproduced by budding, as performed by us in our experimental orchard located near Modesto, Calif., and shows that all reproductions of said characteristics run true to form and are established and transmitted through succeeding propagations.

SUMMARY OF THE VARIETY

The new and distinct variety of peach tree is of large size, vigorous, semi-upright growth and is a regular and productive bearer of large, yellow flesh, clingstone fruit with good flavor and eating quality. The fruit of the new variety is further characterized by having firm flesh with the ability to be shipped to long distance markets and in comparison to the commercial peach Spring Lady (U.S. Plant Pat. No. 4,661), which matures in the same maturity season, the new variety has fruit with more attractive red skin color and heavier production of larger size fruit.

BRIEF DESCRIPTION OF THE PHOTOGRAPH

The accompanying photograph shows a reproduction of typical specimens of the foliage and fruit of our new variety of peach tree. The upper and lower surface of the leaves are shown as well as an exterior and sectional view of the fruit divided in the suture plane to reveal flesh coloration, pit cavity and a stone remaining in place. The photograph was taken shortly after picking the fruit at maturity (firm ripe) and the colors are as nearly true as is reasonably possible in a color representation of this type.

DESCRIPTION OF THE VARIETY

The botanical description of the present new variety of peach tree, its flowers, foliage and fruit is based on observations of specimens grown near Modesto, Calif., with color terminology (except those in common terms) in accordance with Reinhold Color Atlas by A. Kornerup and J. H. Wansher.

Tree:
- *Size.*—Large.
- *Vigor.*—Vigorous.
- *Density.*—Medium dense.
- *Form.*—Semi-upright.
- *Production.*—Productive.
- *Bearer.*—Regular.

Trunk:
- *Size.*—Medium stocky.
- *Texture.*—Medium shaggy.
- *Color.*—Brown to coffee brown (5-E-7) to (5-F-7).

Branches:
- *Size.*—Medium.
- *Surface.*—Smooth to medium rough, varies with age of growth.
- *Lenticels.*—Numerous. Large size.
- *Color.*—Light brown to brown (5-D-7) to (5-D-8).

Leaves:
- *Size.*—Large. Average length — 6½". Average width — 1½".
- *Surface.*—Smooth.
- *Margin.*—Crenate.
- *Petiole.*—Average length — ½". Medium thickness.
- *Glands.*—Reniform. Average number 3, varies from 2 to 4. Located on base of leaf blade and upper portion of petiole.
- *Form.*—Lanceolate. Pointed.
- *Color.*—Upper surface — Green to deep green (29-F-5) to (29-F-7). Lower surface — light green to dull green (29-E-5) to (29-E-6).

Flower buds:
- *Size.*—Large.
- *Form.*—Plump.

*Pubescence.*—Pubescent.

Flowers:

*Size.*—Large — showy.

*Blooming period.*—Mar. 5, 1993 to Mar. 10, 1993. Varies slightly due to weather variation.

*Pollen.*—Present.

*Color.*—Pink.

Fruit:

*Maturity when described.*—Firm ripe.

*Date of first picking.*—May 23, 1993.

*Date of last picking.*—May 29, 1993.

*Size.*—Large. Average diameter axially — 3". Average transversely in suture plane — 3".

*Form.*—Nearly globose — some fruit slightly larger on one side.

*Suture.*—Shallow — extends from base to apex.

*Ventral surface.*—Nearly rounded.

*Cavity.*—Rounded — slightly elongated in suture plane. Average depth — ½". Average breadth — ¾".

*Base.*—Retuse.

*Apex.*—Usually slightly pointed — varies from slightly pointed to round.

Skin:

*Thickness.*—Medium.

*Texture.*—Medium — tenacious to the flesh.

*Tendency to crack.*—None.

*Down.*—Moderate to heavy.

*Color.*—Yellow ground color (4-A-5) to (4-A-7). Overspread with red (9-B-8) to (10-B-8).

Flesh:

*Ripens.*—Relatively even, slightly earlier near apex.

*Texture.*—Firm.

*Fibers.*—Small, tender.

*Juice.*—Moderate.

*Aroma.*—Moderate.

*Amygdalin.*—Undetected.

*Flavor.*—Good — a good balance between sugar and acid.

*Eating quality.*—Good.

*Color.*—Yellow (4-A-4) to (4-A-7). Pit cavity — amber yellow (4-B-6).

Stone:

*Type.*—Clingstone.

*Size.*—Large. Average length — 1⅝". Average width — 1⅛". Average thickness — ⅝".

*Apex.*—Cuspidate.

*Base.*—Usually straight, varies from rounded to straight.

*Form.*—Obovoid.

*Sides.*—Mostly equal — varies from equal to unequal.

*Surface.*—Irregularly furrowed toward apex, pitted toward base — pits vary from elongated to round.

*Ridges.*—Rounded.

*Tendency to split.*—Very slight.

*Color.*—Light brown to brown (6-C-4) to (6-C-5).

Use: Dessert.

*Market.*—Local and long distance.

Keeping quality: Good.

Shipping quality: Good.

The present new peach tree, its flowers, foliage and fruit herein described, may vary in slight detail due to soil type, cultural practices and climatic conditions under which the variety may be grown. The present description is that of the variety grown under the ecological conditions prevailing near Modesto, Calif.

We claim:

1. A new and distinct variety of peach tree, substantially as illustrated and described, characterized by its large size, vigorous, semi-upright growth and by being a productive and regular bearer of large, firm, yellow flesh, clingstone fruit with an attractive red skin color; the fruit is further characterized by having good eating, keeping and shipping qualities and in comparision to the commercial peach variety Spring Lady (U.S. Plant Pat. No. 4,661), which matures in the same maturity season, the new variety bears larger size fruit with heavier production.

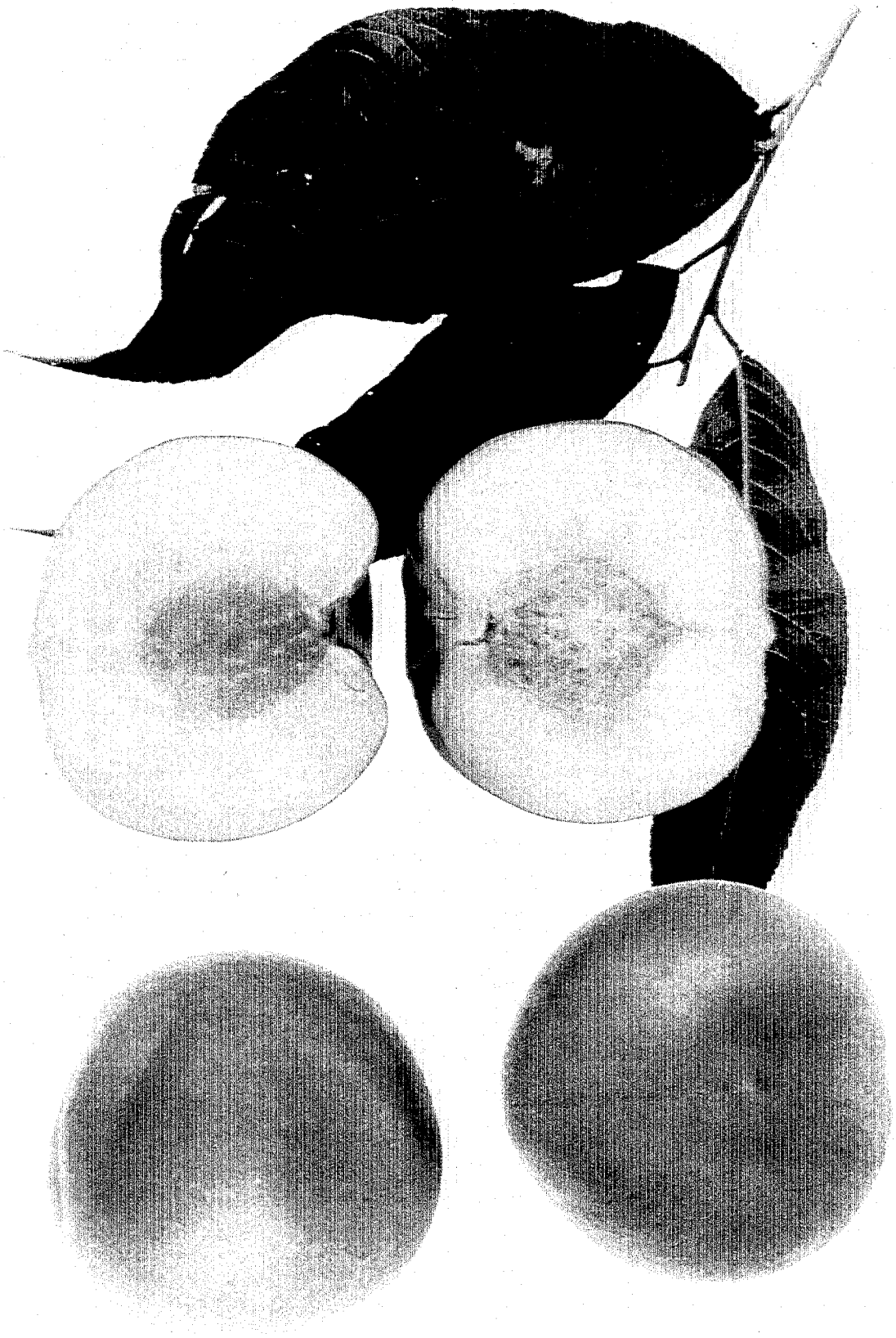

* * * * *